United States Patent [19]
Andersen

[11] Patent Number: 5,919,164
[45] Date of Patent: *Jul. 6, 1999

[54] CONVERTIBLE CATHETER AND THE LIKE

[75] Inventor: Erik C. Andersen, Roskilde, Denmark

[73] Assignee: Boston Scientific Corporation, Natick, Mass.

[ * ] Notice: This patent is subject to a terminal disclaimer.

[21] Appl. No.: 09/083,576

[22] Filed: May 22, 1998

Related U.S. Application Data

[63] Continuation of application No. 08/595,874, Feb. 6, 1996, Pat. No. 5,755,685, which is a continuation of application No. 08/219,120, Mar. 29, 1994, Pat. No. 5,489,271.

[51] Int. Cl.[6] .................................................. A61M 29/00
[52] U.S. Cl. ..................... 604/102; 604/170; 604/282; 606/194
[58] Field of Search ............................. 604/96–103, 164, 604/170, 280, 282; 606/192–196

*Primary Examiner*—Wynn Wood Coggins
*Assistant Examiner*—Deborah Blyveis
*Attorney, Agent, or Firm*—Fish & Richardson P.C.

[57] ABSTRACT

A stylet and hub assembled for stiffening a catheter in rapid exchange mode. The catheter guidewire lumen has a side port associated with a bi-stable guide element that lies across the lumen. A disengageable feature assembly limits insertion of the stylet into the lumen in rapid exchange mode. To convert from rapid exchange mode, disengagement of the disengageable feature enables the stylet to displace the guide element, clearing the guidewire lumen and enabling guidewire or other device to extend throughout the lumen. The stylet has a long proximal portion, a relatively short portion tapering distally to a smaller diameter, and enlarged end. The guide element is formed by plastic deformation of the catheter wall. The disengageable feature is in a removable housing having an end cap that can be replaced with a syringe for flushing liquid along the stylet. A balloon, preferably a PTCA balloon, is mounted on the catheter.

14 Claims, 6 Drawing Sheets

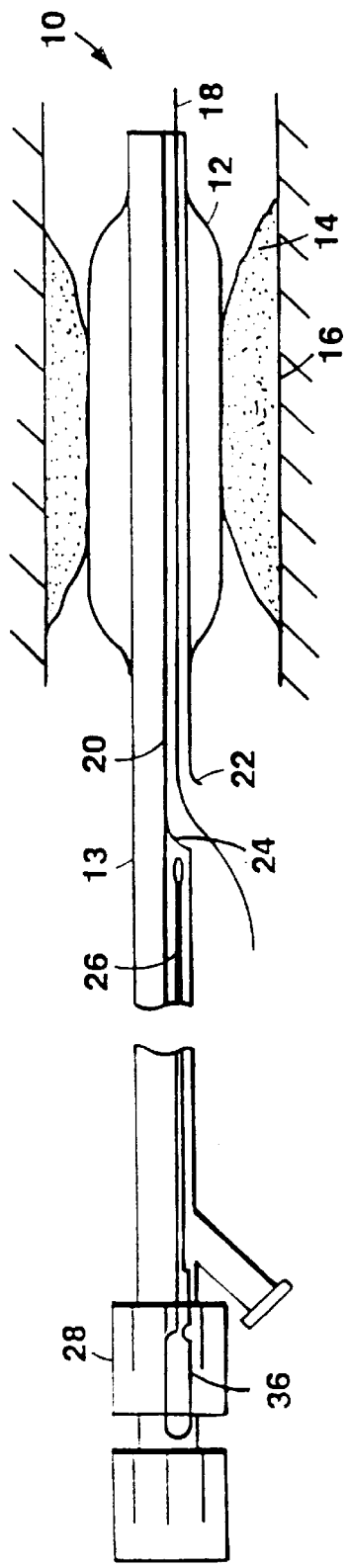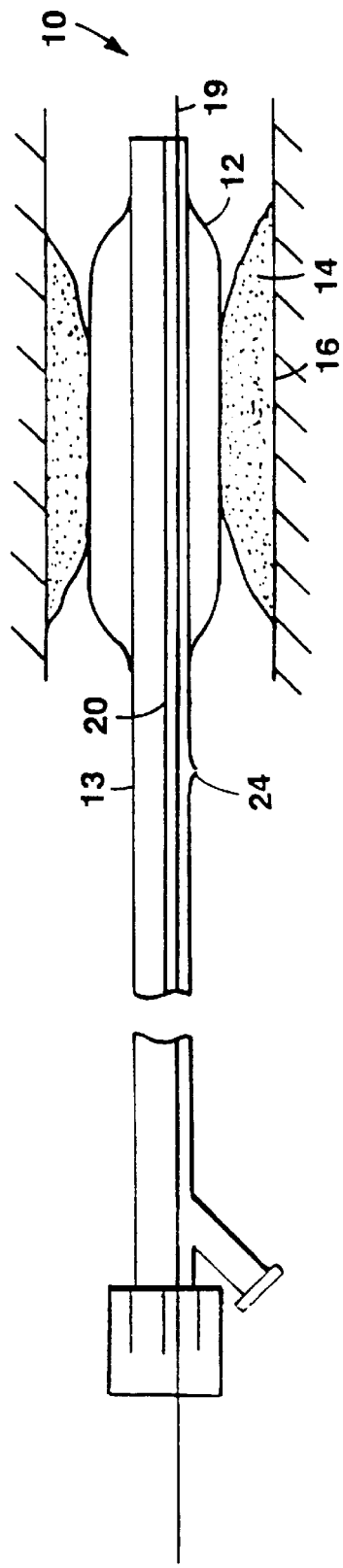

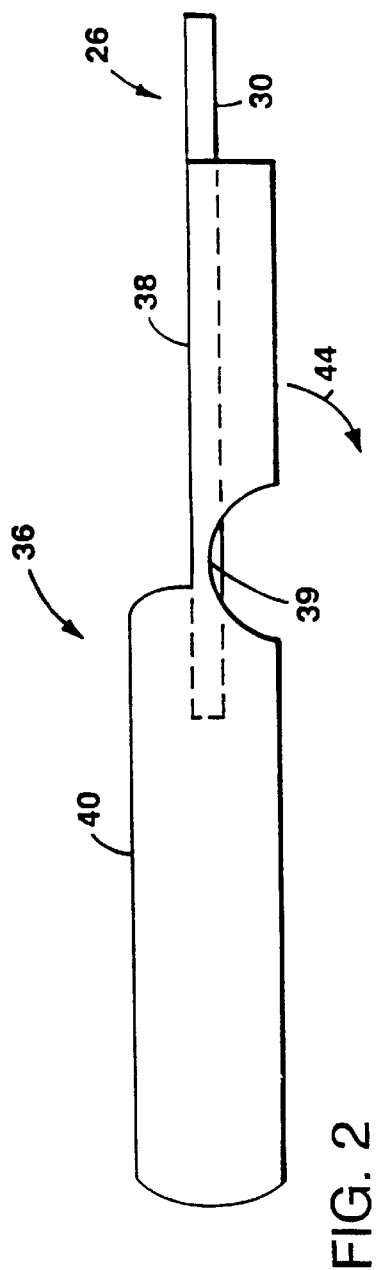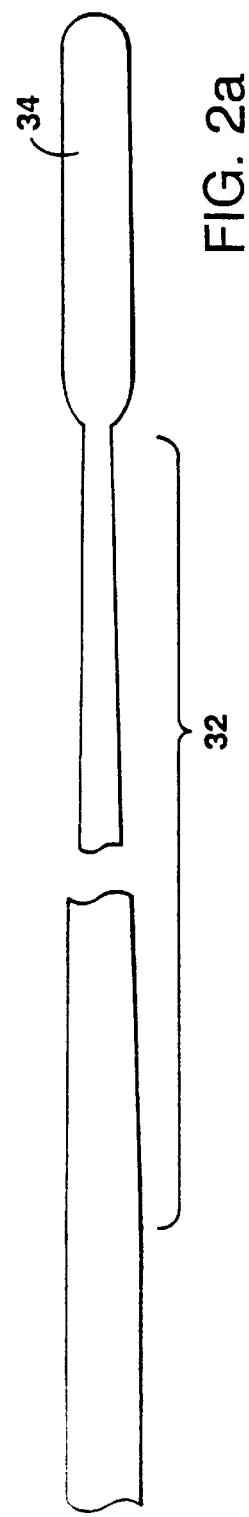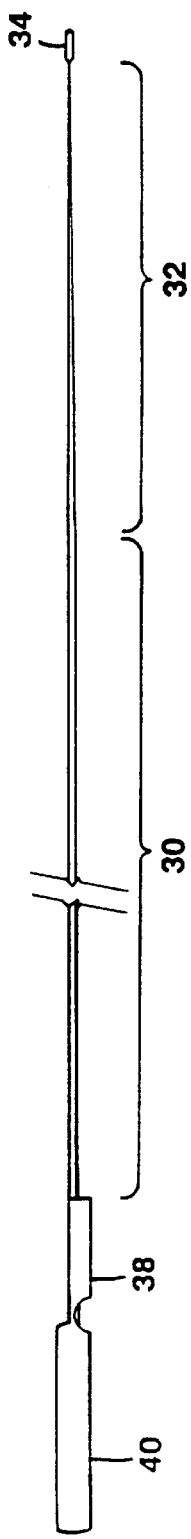

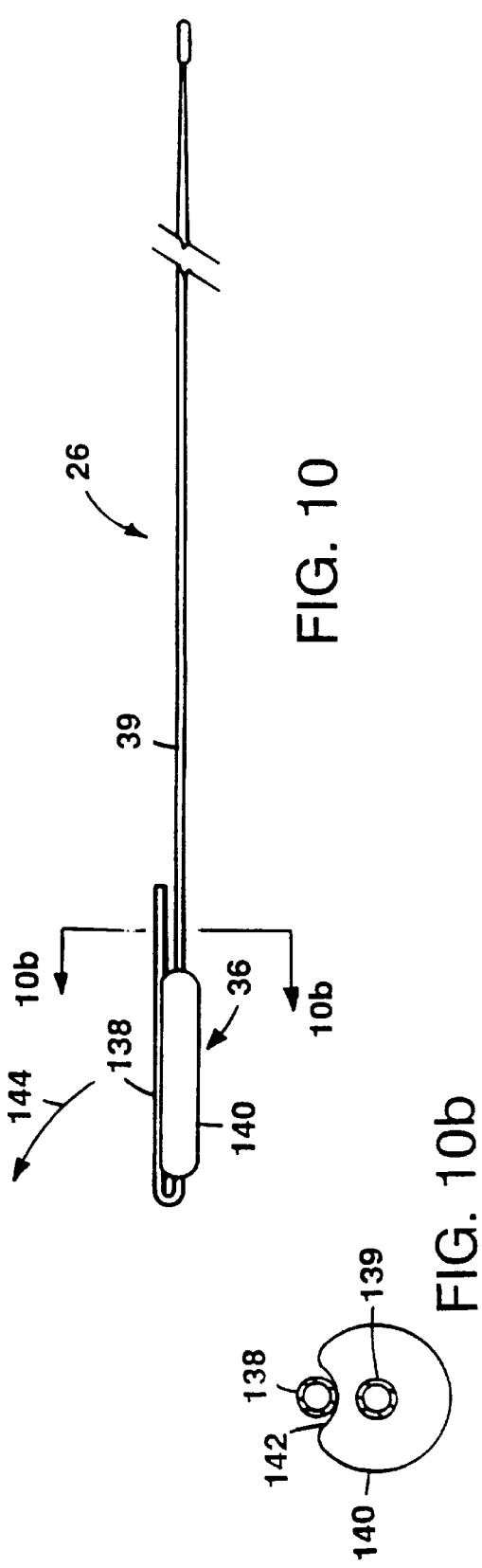

CONVERTIBLE CATHETER AND THE LIKE

REFERENCES TO RELATED APPLICATIONS

This is a continuation of U.S. application Ser. No. 08/595,874, filed Feb. 6, 1996, U.S. Pat. No. 5,755,685, which is a continuation of Ser. No. 08/219,120, filed Mar. 29, 1994, U.S. Pat. No. 5,489,271.

BACKGROUND OF THE INVENTION

This invention relates to convertible catheters and has particular application to percutaneous transluminal angioplasty and the ability to convert a rapid exchange catheter into a conventional over-the-wire catheter.

It has been known to have PTCA catheters that are convertible from a rapid exchange mode to a conventional over-the-wire mode but there have been drawbacks in the convenience and rapidity of their use.

SUMMARY OF THE INVENTION

It is realized, according to the invention, that by providing a stylet and hub assembled for stiffening the catheter in rapid exchange mode with the assembly having a disengageable feature the catheter may be converted from rapid exchange mode to over-the-wire mode using the stylet.

One aspect of the invention relates to a catheter assembly comprising a catheter and a stylet, the catheter comprising a shaft having a guidewire lumen extending from proximal to distal regions of the catheter, the catheter suitable for placement alternatively in rapid exchange mode and over-the-wire mode. The catheter has a side port entering into the guidewire lumen at a position in the distal region of the catheter proximal of the distal end of the catheter to enable use in rapid exchange mode, and the catheter has a guide element secured adjacent to the proximal portion of the side port, this guide element having first and second positions, in its first position the guide element extending downwardly across the guidewire lumen in obstructing position to deflect out of the side port a guidewire being inserted into the guidewire lumen through the distal end of the catheter, and in its second position the guide element lying generally along the body of the catheter out of lumen-obstructing position. The stylet is sized during use of the catheter in rapid exchange mode to lie in the proximal portion of the guidewire lumen of the catheter with its distal end proximal of the guide element to enhance the pushability of the corresponding portion of the catheter. According to this aspect of the invention the improvement is made wherein the catheter assembly includes a disengageable stylet stop structure, the stop structure constructed to limit the distance of insertion of the stylet into the guidewire lumen to a first stylet position in which the distal end of the stylet lies proximal of the guide element for use during rapid exchange mode, the stop structure being disengageable to permit the stylet to be advanced further into the guidewire lumen to engage the guide element, with the stop structure disengaged, the stylet sized and constructed to enable advancement of the stylet to displace the guide element from its first position to its second position after which the stylet can be removed from the guidewire lumen, whereby when it is desired to convert the catheter from rapid exchange mode of use the stylet can be employed to clear the guidewire lumen. This enables a conventional guidewire or other device to extend throughout the length of the guidewire lumen.

Preferred embodiments of this aspect of the invention include one or more of the following features.

The stylet has a distal bulbous end portion larger than the portion of the stylet immediately proximal thereof, the bulbous end portion being constructed to engage and displace the guide element from its first position to its second position while avoiding detrimentally affecting the flexibility of the catheter when the stylet is in place during rapid exchange mode of use.

The stylet has a long proximal first portion having a selected first diameter that imparts sufficient stiffness to the catheter to enable the catheter to be pushed into place, and a relatively short second portion distal of the proximal first portion, the second portion tapering distally to a smaller diameter, the second portion serving as a relatively soft leading portion.

The guide element is an integral part of the catheter and has bi-stable characteristics such that it resides with stability in whichever of the first and second positions it is placed.

The guide element is formed by the method of introducing a mandrel into the guidewire lumen of the catheter, advancing the mandrel to the position the guide element is to be located, heating the catheter in the vicinity of the guide element position to thermoforming temperature, and forming the guide element from the wall material of the catheter by pressing a forming instrument against a corresponding portion of the wall toward the mandrel, the engaged portion of the catheter wall thereby undergoing plastic deformation to form the guide element.

The disengageable stop structure comprises a forward extension from a handle associated with the proximal portion of the stylet, the extension, when in effective position, constructed to butt forwardly against a surface associated with the catheter to limit the amount of insertion of the stylet into the guidewire lumen, and with the extension removed from effective position, the stylet being advanceable further into the guidewire lumen. Preferably the extension is formed integrally with the handle, the extension being capable of bending to remove it from the effective position and the extension is connected to the handle by a hinge or the extension is constructed to be broken off and removed from the handle.

In another preferred embodiment the disengageable stop structure is a pivotable wire bail.

The disengageable stop structure is disposed in a housing, this housing being removable when it is desired to access the stylet. Preferably the housing has a removable proximal end cap capable of being removed and replaced with a syringe to enable introduction of flushing liquid under pressure along the stylet.

A balloon is mounted about the catheter shaft distal of the side port and proximal of the distal end of the catheter, the shaft including an inflation lumen extending from the proximal end of the catheter to the interior of the balloon. Preferably the balloon is a PTCA balloon.

Another aspect of the invention concerns a method of converting a catheter from rapid exchange mode to over-the-wire mode using a stylet. The catheter comprises a shaft having a guidewire lumen extending from proximal to distal regions of the catheter, the catheter having a side port entering into the guidewire lumen at a position in the distal region of the catheter proximal of the distal end of the catheter to enable use in rapid exchange mode. The catheter has a guide element secured adjacent to the proximal portion of the side port, this guide element having first and second positions, in its first position the guide element extending downwardly across the guidewire lumen in obstructing position to deflect out of the side port a guidewire being inserted into the guidewire lumen through the distal end of the catheter, and in its second position the guide element lying generally along the body of the catheter out of lumen-obstructing position. The stylet is sized during use of the catheter in rapid exchange mode to lie in the proximal portion of the guidewire lumen of the catheter with distal end proximal of the guide element to enhance the pushability of the corresponding portion of the catheter. According to this aspect of the invention the catheter system defined by the catheter and the stylet includes a disengageable stylet stop structure, the stop structure constructed to limit the distance of insertion of the stylet into the guidewire lumen to a first stylet position in which the distal end of the stylet lies proximal of the guide element for use during rapid exchange mode, the stop structure being disengageable to permit the stylet to be advanced further into the guidewire lumen to engage the guide element, with the stop structure disengaged, the stylet sized and constructed to enable advancement of the stylet to displace the guide element from its first position to its second position after which the stylet can be removed from the guidewire lumen. When it is desired to convert the catheter from rapid exchange mode of use to conventional over-the-wire mode of use the guidewire is removed, the disengageable stop is disengaged, the stylet is advanced to engage the guide element and displace it from its first position to its second position, the stylet is then removed to clear the guidewire lumen to enable its use for other purposes. In one preferred embodiment of use, a second guidewire is extended throughout the length of the guidewire lumen for use of the catheter in conventional over-the-wire mode.

BRIEF DESCRIPTION OF THE DRAWINGS

FIGS. 1 and 1a are diagrammatical side views of an embodiment of the invention in use, respectively, in rapid exchange and over-the-wire modes of use;

FIGS. 2 and 2a are, respectively, enlarged side views of the proximal end portion and the distal end portion of the stylet of the embodiment; FIG. 2b is a side view of the distal end portion of the stylet of the embodiment on a reduced scale;

FIGS. 6, 7, 8, and 9 are enlarged cross-sectional views of the hub portion of the embodiment at successively different stages of the conversion of the catheter from rapid exchange to over-the-wire mode of use, while

FIG. 10 is a side view of an alternative embodiment of the stylet to that of FIGS. 2–2b with the disengageable portion in stylet limiting position, while FIG. 10a is a side view of the embodiment with the disengageable portion in stylet advancing position; FIG. 10b is a cross-sectional view of the embodiment taken along line 10b—10b in FIG. 10.

DESCRIPTION OF THE PREFERRED EMBODIMENT

Figure 3:
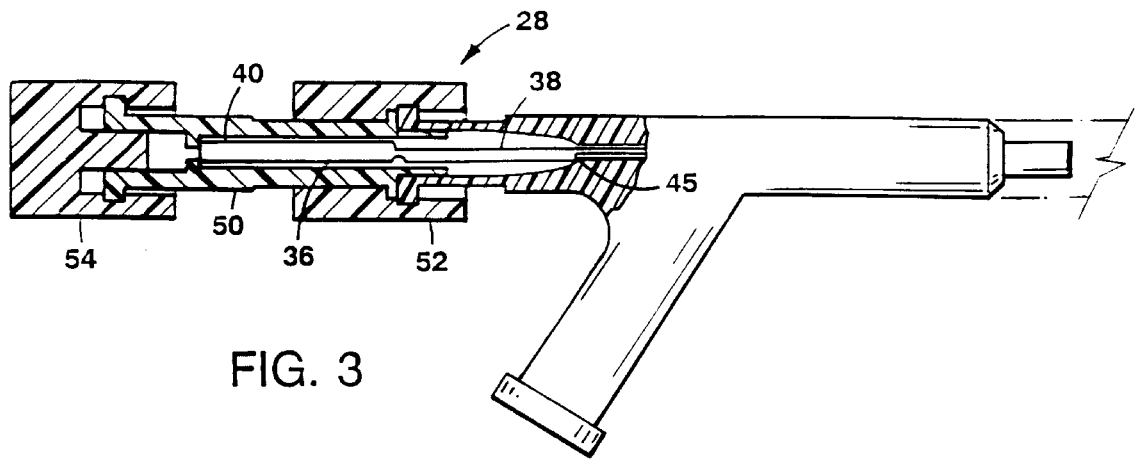
FIG. 3 is an enlarged cross-sectional view of the hub portion of the embodiment.

The figures show a device according to the present invention positioned at a diseased site 14 within a blood vessel 16 for performing balloon dilation on the diseased site. The device can be used for percutaneous transluminal angioplasty alternately in rapid exchange mode, i.e., advancing a device over a guidewire when only the distal portion of the device encloses the guidewire, FIG. 1, and over the wire mode, FIG. 1a.

Referring to FIG. 1, PTCA balloon catheter device 10 has balloon 12 mounted on catheter shaft 13. Shaft 13 is a plastic extrusion having three lumens, i.e., a guidewire lumen 20, a balloon inflation lumen 21 (see FIG. 5), and a third lumen 23 in which a nitinol wire permanently resides (see FIG. 5).

In use in the rapid exchange mode depicted in FIG. 1, a guidewire 18 extends through the distal end of the guidewire lumen and exits from the shaft through a side port 22 distal of a guide element 24 formed of the shaft material. A stylet 26 is shown inside guidewire lumen 20 with its distal end proximal of guide element 24 and its proximal end bonded to a handle 36 terminating within the structure of hub assembly 28.

Referring to FIG. 1a, in over-the-wire mode, the guide element 24 is raised into general alignment with the wall of the shaft, and stylet 26 and guidewire 18 are replaced with a guidewire 19 which extends through guidewire lumen 20 from the proximal to distal regions of device 10.

Referring to FIGS. 2–2b, stylet 26 is constructed from suitable wire, e.g., nitinol, with a proximal section 30 having a diameter, e.g., 0.48 mm, and length, e.g., 1340 mm. The stylet tapers over a second region 32, e.g., 75 mm, to a diameter, e.g., 0.23 mm, near its distal end. The distal end of the stylet consists of an enlarged end ball 34, having a diameter, e.g., 0.48 mm, and a length. e.g., 3 mm. The proximal end of stylet 26 is bonded to a handle 36 which has a disengageable feature. The handle 36 has forward extension 38 and proximal section 40. Extension 38 is joined to section 40 by a thin section 39 enabling extension 38 to be broken off by rotating along arrow 44. The stylet is constructed to add desirable stiffness to the catheter in the rapid exchange mode of use with the tapered region 32 providing stiffening but to a lesser degree than the proximal section 30 to enable flexibility and to avoid damage to the catheter during stylet introduction into the catheter.

Referring to FIG. 3, during the rapid exchange mode of use, an extension tube 50 of the hub assembly 28 fits over the stylet handle 36 with the disengageable forward extension 38 secured by a fitting 52. A cap 54 fits over the proximal end of tube 50. The tube 50 incorporates a ledge 45 that confines the distal end of forward extension 38 of the stylet handle 36 while the proximal end of section 40 of the handle is confined within tube 50. Thus the distal end of the stylet is positioned proximal of guide element 24 and cannot engage guide element 24.

Figure 4:
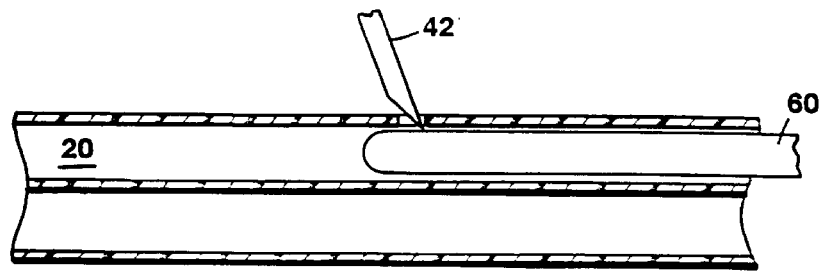
FIGS. 4–4a illustrate a method of making the guide element of the embodiment.
Figure 4A:
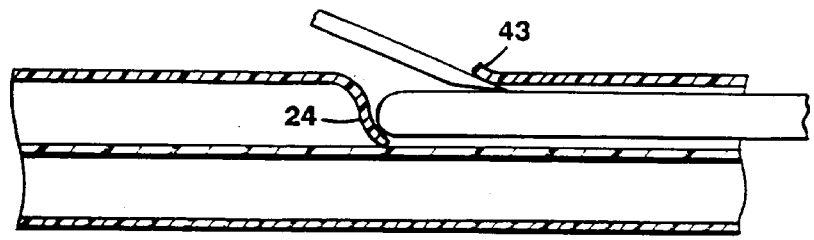
Figure 5:
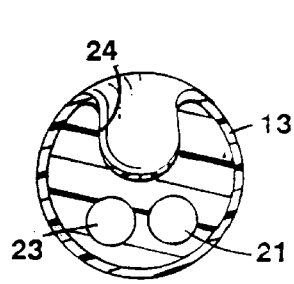
FIGS. 5–5a are end views of the embodiment in their different modes of use.
Figure 5A:
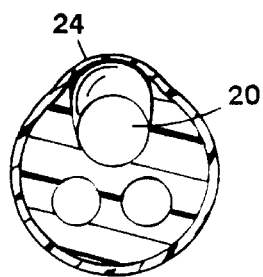

Referring to FIG. 4, during manufacture, guide element 24 is formed of the shaft material by introducing a mandrel 60 into the distal end of guidewire lumen 20 with the end of the mandrel positioned where the guide element is to be located. Shaft 13 is then punctured through a section of the wall of the shaft using a hypodermic needle 42 which is ground to a 30° tip. The mandrel is then advanced with the section of the shaft that is to form the guide element pushed into a position where it blocks the guidewire lumen, FIG. 4a. The needle is wedged between the shaft and the mandrel to flare the shaft. The flare 43 facilitates guidewire exiting through the side port. The assembly is held in position with a silicone rubber tube or the like (not shown) while the balloon catheter is heated in the vicinity of the guide element position. The heating is to a sufficient degree to cause the portion of the shaft that is formed into the guide element and the portion of the shaft that is flared to undergo plastic deformation. Upon cooling the guide element 24 has bi-stable properties. Referring to FIGS. 1, 5 and 6a, the guide element is stable in a position where it is obstructing the guidewire lumen 20. Referring to FIGS. 1a, 5a and 7a, in the second stable position the guide element is in non-obstructing position, lying along the wall of the catheter shaft. In this position, as shown in FIG. 1a, the catheter is employed in over-the-wire mode with guide wire 19 extending throughout the guidewire lumen 20, without hindrance by the guide element. Obviously, the now-open guide wire lumen can be used for other purposes as well, for instance, introducing contrast medium, or a pressure detecting probe.

In preparation for rapid exchange mode, the guidewire is back loaded into the distal end of the guidewire lumen 20 and the guiding element serves to deflect and guide the guidewire out of the side port.

In operation, the balloon catheter 10 with guidewire 18 and stylet 26 positioned in rapid exchange mode is flushed by removing cap 54 and fitting a syringe (not shown) onto the distal end of extension tube 50. A guiding catheter (not shown) is placed in the body and catheter 10, with the guidewire in place, is advanced through the guiding catheter to diseased site 14. Guidewire 18 is then advanced forward of the catheter to the diseased site and balloon catheter 12 is then advanced over the guidewire and positioned to perform balloon dilation in rapid exchange mode.

It is found that with the stylet in place for rapid exchange mode of use, due to its limited axial extent, the enlarged end of the stylet does not detrimentally affect the flexibility of the catheter.

Figure 6:
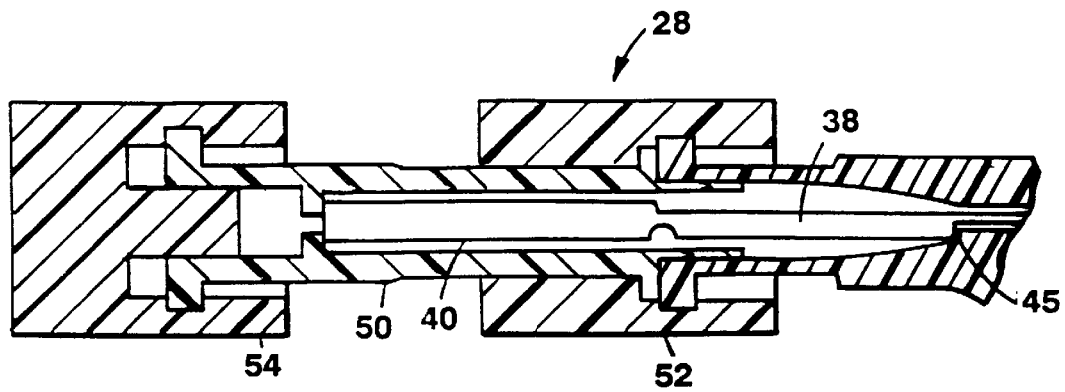
Figure 6A:
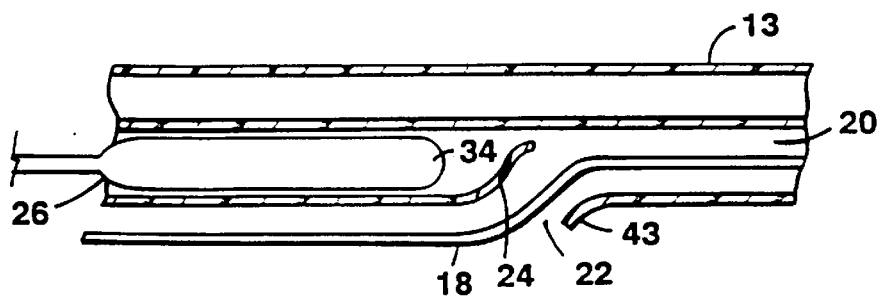
FIGS. 6a, 7a, 8a, and 9a are corresponding views of the side port region of the embodiment at the respective different stages.
Figure 7:
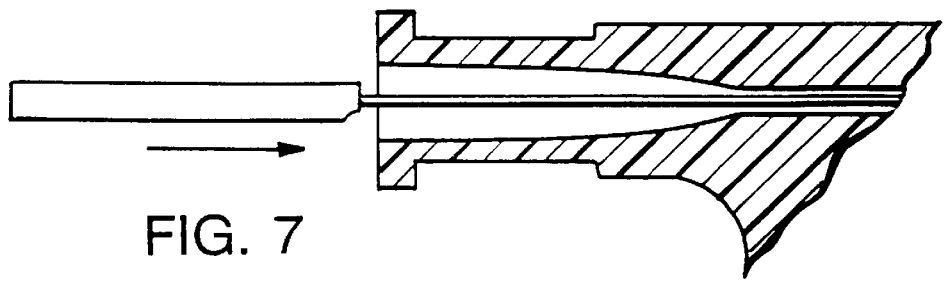
Figure 7A:
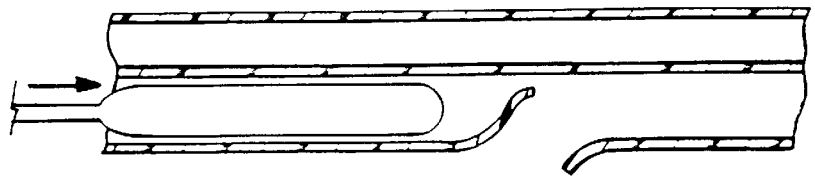
Figure 8:
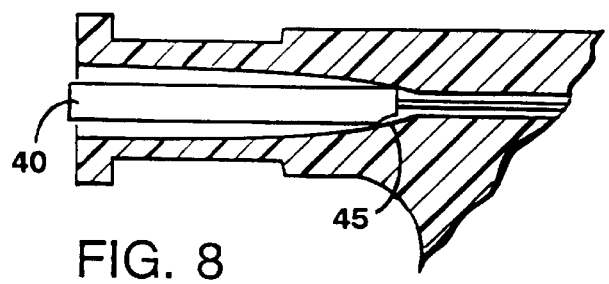
Figure 8A:
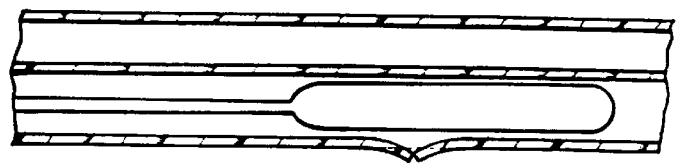

Referring to FIGS. 6–6a, in rapid exchange mode, forward extension 38 of handle 36 limits stylet advancement to a position proximal of guide element 24 by engagement against ledge 45. If a new guidewire is desired, guidewire 18 is pulled proximally out of the guidewire lumen through the side port to remove it. Fitting 52 is then removed to allow stylet 26 to be pulled proximally. At this point the disengageable forward extension 38 is broken from the stylet handle 36 so it no longer prevents stylet advancement.

Figure 9:
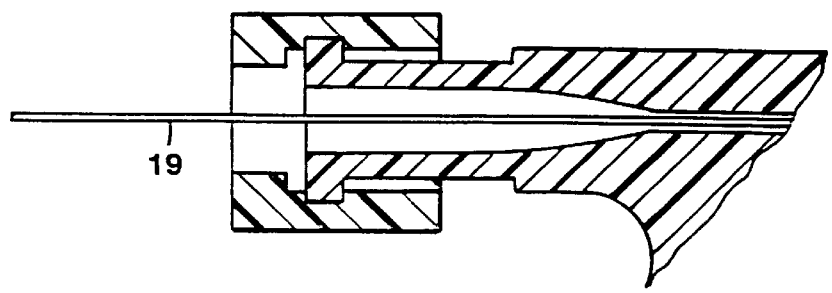
Figure 9A:

Referring to FIGS. 7–7a and 8–8a, stylet 26, thus modified, is then pushed distally until section 40 engages ledge 45. The enlarged distal end of the stylet functions to ensure that the guiding element is forcefully engaged during advance of the stylet. In this movement the stylet pushes guide element 24 which deflects and comes to rest in its other stable position, out of lumen-blocking position as it is advanced. Referring to FIGS. 9–9a, the stylet is then removed leaving the full length of the guidewire lumen clear for the introduction of guidewire 19 in over-the-wire mode or for other uses as mentioned above.

If a catheter exchange is desired, balloon catheter 12 is removed leaving guidewire 19 in place. A new catheter can then be advanced over the guidewire in the traditional over-the-wire manner.

In another embodiment, the forward extension 38 may be joined to the proximal portion 40 by a living hinge at thin section 39 (see FIG. 2) that allows extension 38 to be folded rearwardly to permit the additional advance of the stylet.

Referring to FIGS. 10–10b, in another embodiment the disengageable portion of stylet handle 36 may be in the form, e.g., of a metal bail 138 made from, e.g., soft stainless steel, that may be rotated along arrow 144 from a forward projecting position (see FIG. 10), in which it limits the stylet from engaging the guiding element 24, to a rearward projecting position (see FIG. 10a), in which the handle permits forward movement of the stylet to engage and displace the guiding element 24. Section 139 of stylet 26 made from, e.g., nitinol, extends from the distal end of molded bail connector 140 and wire bail 138 extends from the proximal end, portions not seen being embedded in the molded connector in a secure relationship. As best shown in FIG. 10b, bail connector 140 includes a longitudinal depression 142 on the exterior of molded connector 140 in which wire bail 138 resides while in stylet limiting position.

In another embodiment the disengageable feature may be bonded to hub assembly 28 rather than handle 36.

Other embodiments will occur to those skilled in the art and are within the following claims:

What is claimed is:

1. A catheter assembly comprising a catheter and a stylet, said catheter comprising a shaft having a guidewire lumen extending from proximal to distal regions of the catheter, said catheter suitable for placement alternatively in rapid exchange mode and over-the-wire mode, said catheter having a side port entering into said guidewire lumen at a position in the distal region of the catheter proximal of the distal end of the catheter to enable use in said rapid exchange mode, said catheter having a guide element secured adjacent to the proximal portion of said side port and having first and second positions, in its first said position said guide element extending downwardly across said guidewire lumen in obstructing position to deflect out of the side port a guidewire being inserted into said guidewire lumen through the distal end of the catheter, in its second said position said guide element lying generally along the body of the catheter out of lumen-obstructing position, and said stylet sized during use of the catheter in rapid exchange mode to lie in the proximal portion of said guidewire lumen of said catheter with distal end proximal of said guide element to enhance the pushability of the corresponding portion of said catheter, the improvement wherein said catheter assembly includes a disengageable stylet stop structure, said stop structure constructed to limit the distance of insertion of said stylet into said guidewire lumen to a first stylet position in which the distal end of the stylet lies proximal of said guide element for use during said rapid exchange mode, said stop structure being disengageable to permit said stylet to be advanced further into said guidewire lumen to engage said guide element, with said stop structure disengaged, said stylet sized and constructed to enable advancement of said stylet to displace said guide element from its said first position to its said second position after which said stylet can be removed from said guidewire lumen, whereby when it is desired to convert said catheter from rapid exchange mode of use, said stylet can be employed to clear the guidewire lumen.

2. The catheter system of claim 1 wherein said stylet has a distal bulbous end portion larger than the portion of said stylet immediately proximal thereof, said bulbous end portion being constructed to engage and displace said guide element from its said first position to its said second position while avoiding detrimentally affecting the flexibility of said catheter when the stylet is in place during rapid exchange mode of use.

3. The catheter system of claims 1 or 2 wherein said stylet has a long proximal first portion having a selected first diameter that imparts sufficient stiffness to said catheter to enable the catheter to be pushed into place, and a relatively short second portion distal of said proximal first portion, said second portion tapering distally to a smaller diameter, said second portion serving as a relatively soft leading portion.

4. The catheter system of claim 1 wherein said guide element is an integral part of said catheter and has bistable characteristics such that it resides with stability in whichever of said first and second positions it is placed.

5. The catheter system of claim 1 or 4 wherein said guide element is formed by the method of introducing a mandrel into the guidewire lumen of said catheter, advancing said mandrel to the position said guide element is to be located, heating said catheter in the vicinity of said guide element position to thermoforming temperature, and forming said guide element from the wall material of said catheter by pressing a forming instrument against a corresponding portion of said wall toward said mandrel, the engaged portion of said catheter wall thereby undergoing plastic deformation to form said guide element.

6. The catheter system of claim 1 wherein said disengageable stop structure comprises a forward extension from a handle associated with the proximal portion of said stylet, said extension, when in effective position, constructed to butt forwardly against a surface associated with said catheter to limit the amount of insertion of said stylet into said guidewire lumen, and with said extension removed from effective position said stylet being advanceable further into said guidewire lumen.

7. The catheter system of claim 6 wherein said extension is formed integrally with said handle, said extension being capable of bending to remove it from said effective position.

8. The catheter system of claim 7 wherein said extension is connected to said handle by a hinge.

9. The catheter system of claim 7 wherein said extension is constructed to be broken off and removed from said handle.

10. The catheter system of claim 1 wherein said disengageable stop structure is a pivotable wire bail.

11. The catheter system of claim 1 wherein said disengageable stop structure is disposed in a housing, said housing being removable when it is desired to access said stylet.

12. The catheter system of claim 11 wherein said housing has a removable proximal end cap capable of being removed and replaced with a syringe to enable introduction of flushing liquid under pressure along said stylet.

13. The catheter system of claim 1 wherein a balloon is mounted about said catheter shaft distal of said side port and proximal of the distal end of said catheter, said shaft including an inflation lumen extending from the proximal end of said catheter to the interior of said balloon.

14. The catheter system of claim 13 wherein said balloon is a PTCA balloon.

* * * * *